(12) United States Patent
Park et al.

(10) Patent No.: US 7,769,135 B2
(45) Date of Patent: Aug. 3, 2010

(54) X-RAY DIFFRACTION WAFER MAPPING METHOD FOR RHOMBOHEDRAL SUPER-HETERO-EPITAXY

(75) Inventors: Yeonjoon Park, Yorktown, VA (US); Sang Hyouk Choi, Poquoson, VA (US); Glen C. King, Yorktown, VA (US); James R. Elliott, Yorktown, VA (US); Albert L. Dimarcantonio, Williamsburg, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 12/288,380

(22) Filed: Oct. 20, 2008

(65) Prior Publication Data

US 2010/0027746 A1 Feb. 4, 2010

Related U.S. Application Data

(60) Provisional application No. 60/980,876, filed on Oct. 18, 2007, provisional application No. 60/980,870, filed on Oct. 18, 2007, provisional application No. 60/980,881, filed on Oct. 18, 2007, provisional application No. 60/980,878, filed on Oct. 18, 2007, provisional application No. 60/980,871, filed on Oct. 18, 2007, provisional application No. 60/980,880, filed on Oct. 18, 2007.

(51) Int. Cl.
*G01N 23/20* (2006.01)
(52) U.S. Cl. .......................................... 378/73; 378/71
(58) Field of Classification Search ................... 378/71, 378/73, 89, 91
See application file for complete search history.

(56) References Cited

U.S. PATENT DOCUMENTS

| 7,558,371 B2* | 7/2009 | Park et al. ...................... 378/71 |
| 2004/0190681 A1* | 9/2004 | Omote .......................... 378/71 |
| 2007/0222034 A1* | 9/2007 | Park et al. ...................... 257/616 |
| 2009/0220047 A1* | 9/2009 | Park et al. ...................... 378/70 |

\* cited by examiner

*Primary Examiner*—Chih-Cheng G Kao
(74) *Attorney, Agent, or Firm*—Robin W. Edwards

(57) ABSTRACT

A new X-ray diffraction (XRD) method is provided to acquire XY mapping of the distribution of single crystals, poly-crystals, and twin defects across an entire wafer of rhombohedral super-hetero-epitaxial semiconductor material. In one embodiment, the method is performed with a point or line X-ray source with an X-ray incidence angle approximating a normal angle close to 90°, and in which the beam mask is preferably replaced with a crossed slit. While the wafer moves in the X and Y direction, a narrowly defined X-ray source illuminates the sample and the diffracted X-ray beam is monitored by the detector at a predefined angle. Preferably, the untilted, asymmetric scans are of {440} peaks, for twin defect characterization.

9 Claims, 4 Drawing Sheets

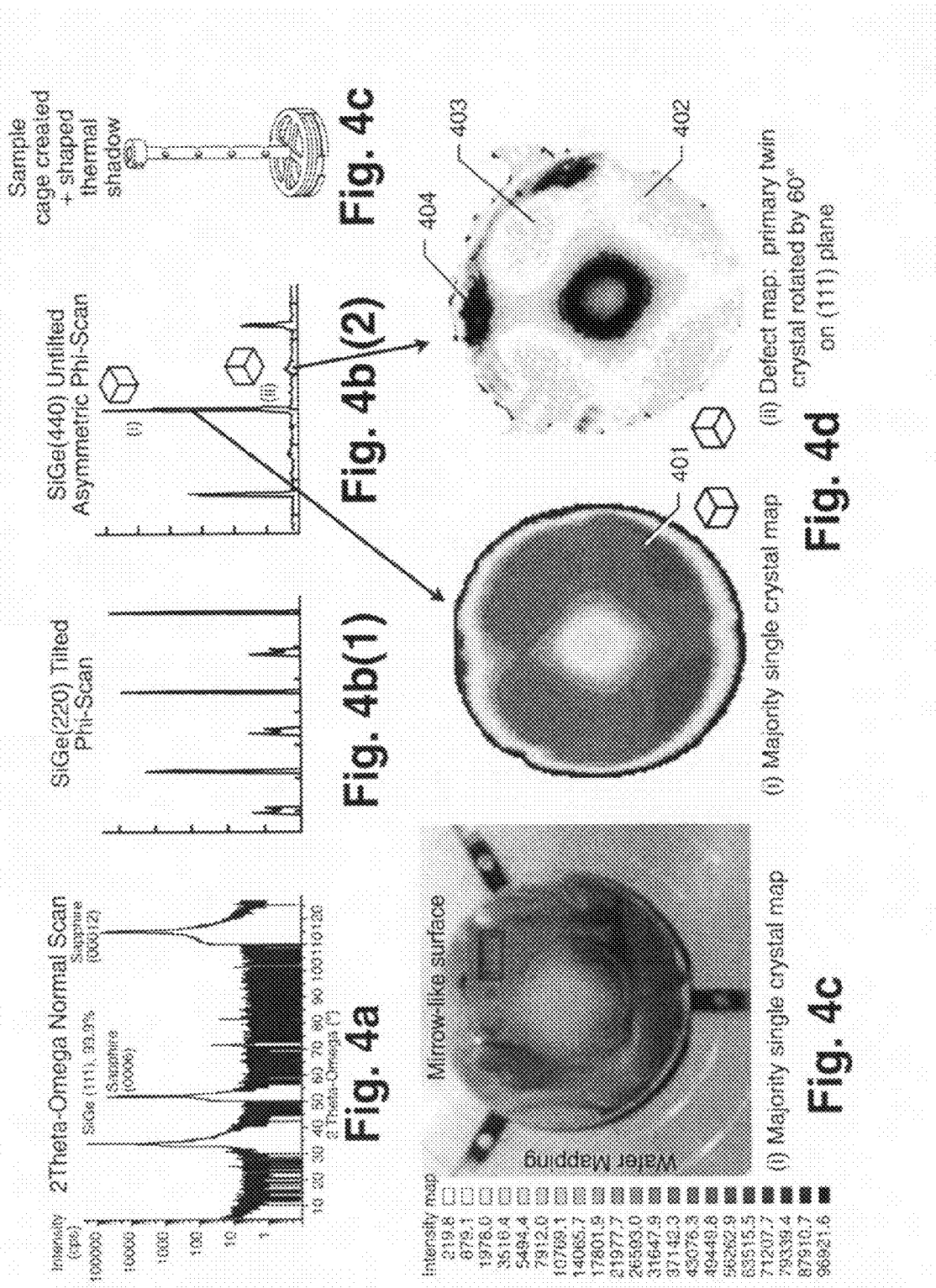

X-RAY DIFFRACTION WAFER MAPPING METHOD FOR RHOMBOHEDRAL SUPER-HETERO-EPITAXY

CROSS-REFERENCE TO RELATED APPLICATIONS

This application claims the benefit of the respective filing dates of, and incorporates by reference the entire respective disclosures of, the following commonly assigned U.S. Provisional Patent Applications: Ser. No. 60/980,876 filed on Oct. 18, 2007, Ser. No. 60/980,881 filed on Oct. 18, 2007, Ser. No. 60/980,878 filed on Oct. 18, 2007, Ser. No. 60/980,880 filed on Oct. 18, 2007, Ser. No. 60/980,871 filed on Oct. 18, 2007 and Ser. No. 60/980,870 filed on Oct. 18, 2007, each of which contains an overlap of inventive entity with the present application. In addition, this application incorporates by reference the entire disclosures of the following commonly assigned nonprovisional U.S. patent applications being filed on the same date as the present application: Ser. No. 12/254,016, entitled "THERMOELECTRIC MATERIALS AND DEVICES;" Ser. No. 12/254,134, entitled "HYBRID BANDGAP ENGINEERING FOR SUPER-HETERO-EPITAXIAL SEMICONDUCTOR MATERIALS, AND PRODUCTS THEREOF;" Ser. No. 12/288,379, entitled "RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS;" Ser. No. 12/254,017, entitled "EPITAXIAL GROWTH OF CUBIC CRYSTALLINE SEMICONDUCTOR ALLOYS ON BASAL PLANE OF TRIGONAL OR HEXAGONAL CRYSTAL;" and Ser. No. 12/254,150, entitled "METHOD OF GENERATING X-RAY DIFFRACTION DATA FOR INTEGRAL DETECTION OF TWIN DEFECTS IN SUPER-HETERO-EPITAXIAL MATERIALS;" each one claiming priority to the above-cited provisional applications.

ORIGIN OF THE INVENTION

The invention was made in part by employees of the United States Government and may be manufactured and used by or for the Government of the United States of America for governmental purposes without the payment of any royalties thereon or therefor.

BACKGROUND OF THE INVENTION

1. Field of the Invention

The present invention relates to defect detection in semiconductor materials. More specifically, the invention concerns a new X-ray Diffraction (XRD) method to acquire XY mapping of the distribution of single crystals, poly-crystals, and twin defects across an entire semiconductor wafer. A reference journal paper by inventors is available at Journal of Crystal Growth, 310 (2008) p. 2724-2731.

2. Description of the Related Art

The disclosure of our commonly filed patent application entitled "Rhombohedral Cubic Semiconductor materials On Trigonal Substrate With Single Crystal Properties and Devices Based on Such Materials," Ser. No. 12/288,379(the "Rhombohedral Cubic Semiconductor Disclosure"), as well as that of other commonly-filed applications, which as stated above have been incorporated into this disclosure by reference, discusses the phenomenon of "twin defects." As explained in those disclosures, when a cubic material layer, such as a layer comprised of group IV, group or group II-VI materials, or alloys thereof, is grown on the (0001) c-plane of a trigonal or hexagonal crystal substrate, the epitaxial layer often contains primary twin defects that are 60° rotated on the (111) plane. The atomic alignment of the cubic crystalline allows poly-type crystalline structures with such 60 degree-rotated twin defects as a result of stacking faults as well as twinning on the interface with the underlying trigonal or hexagonal substrate.

It is desirable to be able to map the distribution of single crystalline material and twin defect material on the wafer, in order to control the quality of epitaxial layers for device fabrication on the wafer. Preferably, the method for such mapping should be nondestructive and should be capable of mapping defects across the entire wafer.

Previously, twin defects were measured with electron microscopy so that only a very small region was characterized. Characterization over entire wafer was not possible with that method. The disclosure of commonly-filed application entitled "Method of Generating X-Ray Diffraction Data for Integral Detection of Twin Defects in Super-Hetero-Epitaxial Materials," Ser. No. 12/254,150, (the "Companion XRD Disclosure"), which as stated above has also been incorporated herein by reference, contains an integral XRD characterization method to measure an averaged property of an entire wafer. However, it does not have a spatial resolution to obtain a wafer mapping with an XY scan.

Accordingly, despite advances in the field, there remains a need for a nondestructive analytic method for defect characterization in two dimensions across wafers of rhombohedral super-hetero-epitaxial materials.

SUMMARY OF THE INVENTION

It is an object of the present invention to provide a nondestructive analytic method for defect characterization in two dimensions across wafers of rhombohedral super-hetero-epitaxial materials.

The present invention provides a new X-ray Diffraction (XRD) method to acquire XY mapping of the distribution of single crystals, poly-crystals, and twin defects across an entire wafer.

In one embodiment, the method is performed with a point or line X-ray source with an X-ray incidence angle to a normal angle which is close to 90°, and in which the beam mask is preferably replaced with a crossed slit. While the wafer moves in the X and Y direction, a narrowly defined X-ray source illuminates the sample and the diffracted X-ray beam is monitored by the detector at a predefined angle. Preferably, the untilted, asymmetric scans are of {440} peaks, for twin defect characterization of cubic semiconductors, including group IV semiconductors (Si, Ge, C, and its alloy), group III-V semiconductors (GaAs, InP, AlAs, etc.), and group II-VI semiconductors (ZnS, CdSe, etc.).

We found that such an XY wafer mapping can detect the distribution of defect regions and single crystal regions on a wafer. Our method can measure an entire wafer with a high spatial resolution (a few nanometers to a few millimeters), with a nearly isotropic and uniform XY scan. This technique can be used as an important defect characterization tool for Rhombohedral Super-Hetero-Epitaxy, including the epitaxial growth of cubic-lattice materials on the basal plane of trigonal-lattice substrate.

Other aspects and advantages of the present invention will be apparent from the accompanying drawings, and the detailed description that follows.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which:

FIG. 4 is a series of panels showing another mapping of the single crystal region and twin defect region of a wafer with a mirror-like surface by 2D XY-scan of wafer with X-ray diffraction from the un-tilted asymmetric phi-scan of SiGe {440} peaks.

DETAILED DESCRIPTION OF THE INVENTION

The following is a detailed description of certain embodiments of the invention chosen to provide illustrative examples of how it may advantageously be implemented. The scope of the invention is not limited to the specific embodiments described, nor is it limited by any specific implementation, composition, embodiment or characterization depicted in the accompanying drawings or stated or described in the invention summary or the abstract. In addition, it should be noted that this disclosure describes a number of methods that each comprise a plurality of steps. Nothing contained in this written description should be understood to imply any necessary order of steps in such methods, other than as specified by express claim language.

In the ensuing description, the well-known Miller indices notation of lattice planes is used. That is, crystal planes are designated by numbers within "( )", groups of similar planes are designated by numbers within "{ }", direction or length is designated by numbers within "[ ]", and groups of similar directions are designated by numbers within "< >".

As described in the "Rhombohedral Cubic Semiconductor Disclosure," we have developed techniques for fabricating a variety of rhombohedrally-grown cubic semiconductors (including group IV semiconductors (Si, Ge, C, and its alloy), group III-V semiconductors (GaAs, InP, AlAs, etc.), and group II-VI semiconductors (ZnS, CdSe, etc.)), on the basal plane of trigonal and hexagonal substrate. We also refer herein to "super-hetero-epitaxial" materials. By "super-hetero-epitaxial" we mean combinations wherein one material having a first crystal structure is grown on a different material having a different crystal structure.

As explained above, it is desirable to be able to provide a method for nondestructive XY mapping of defects in such materials, across the entire wafer. We developed an XY XRD scanning method to accomplish this.

Figure 1:
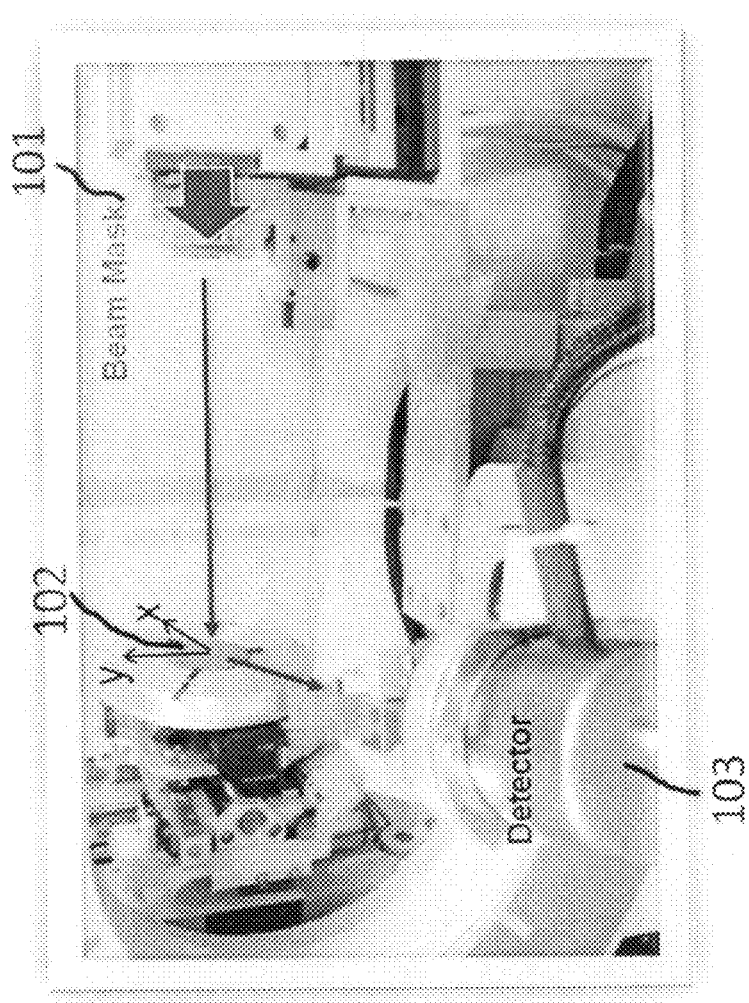
FIG. 1 is a perspective view of an exemplary XRD setup for use in connection with the invention, showing configuration of the source, beam mask, target and detector, providing for asymmetric angles for XY mapping with a point X-ray source.

In summary, we found that XY wafer mapping with a point or line X-ray source with a narrow beam-mask or a crossed slit can detect the distribution of defect regions and single crystal regions on the wafer. In order to do the uniform XY scan on the wafer, it is preferable to set the X-ray incidence angle to a normal angle, close to 90° as shown in FIG. 1. The beam mask 101 can be replaced with a crossed slit (see FIG. 3). While the wafer moves in the X and Y direction (102), a narrowly defined X-ray source illuminates the sample and the diffracted X-ray beam is monitored by the detector 103 at a predefined angle.

Based on numerous calculations and experiments, we found that un-tilted asymmetric X-ray diffraction scans with {440} peaks are the preferred configuration for twin defect characterization of cubic semiconductors, including group IV semiconductors (Si, Ge, C, and its alloy), group III-V semiconductors (GaAs, InP, AlAs, etc.), and group II-VI semiconductors (ZnS, CdSe, etc.).

Other X-ray peaks can be used for the wafer mapping with a non-zero tilt angle (sample tilt angle, $\psi$ (or $\chi$)). However, these XRDs require that the sample be tilted by an angle, and as a result, the XY mapping thereby obtained is not as isotropic and uniform as the un-tilted asymmetric XY-scan of {440} peaks, because the tilt angle causes glancing illumination by the X-ray spot.

The exact calculation of diffraction angles for general (h,k,l) planes is described in many reference books, including the appendix of "Elements of X-ray Diffraction," B. D. Cullity, $2^{nd}$ Ed., Addison-Wesley Publishing Co. Based on the equations presented in that appendix, which is incorporated herein by reference in its entirety, we turn now to the calculation results with a Cu K-$\alpha$ line X-ray source.

For an example of un-tilted (sample tilt angle, $\psi$ (or $\chi$)=0) asymmetric XRD scan of $Si_{0.33}Ge_{0.67}$ alloy, the detector angle (2$\theta$) of (440) peak is 2$\theta$=102.607°. The sample goniometer angle ($\Omega$) has to be set to $\Omega=\theta+\tau$ where $\theta$ is 102.607°/2=51.304° and $\tau$ is the inter-planar angle between (111) plane and (440) plane, such that $\tau$=35.264°. Therefore $\Omega$=51.304°+35.264°=86.568° which is very close to 90°. Accordingly, the XY scan is preferably done at an angle close to the normal direction, and an isotropic and uniform mapping can thereby be achieved. With this configuration, as shown in FIG. 1, the exit angle of X-ray from the surface becomes $\theta-\tau$=16.04°>0° so that it is greater than zero and it provides a valid XRD configuration. On the other hand, many other SiGe peaks like {220} peaks have negative $\theta-\tau$ angle, i.e. $\theta-\tau$=22.969°-35.264°=-12.295°<0°, which cannot be measured with un-tilted asymmetric scan. Therefore, SiGe {440} peaks are the preferred choice for XY wafer mapping for defect characterization. A similar calculation applies to other cubic semiconductor materials in diamond or cubic zinc-blende structure, including GaAs, ZnSe, etc.

Figure 2:
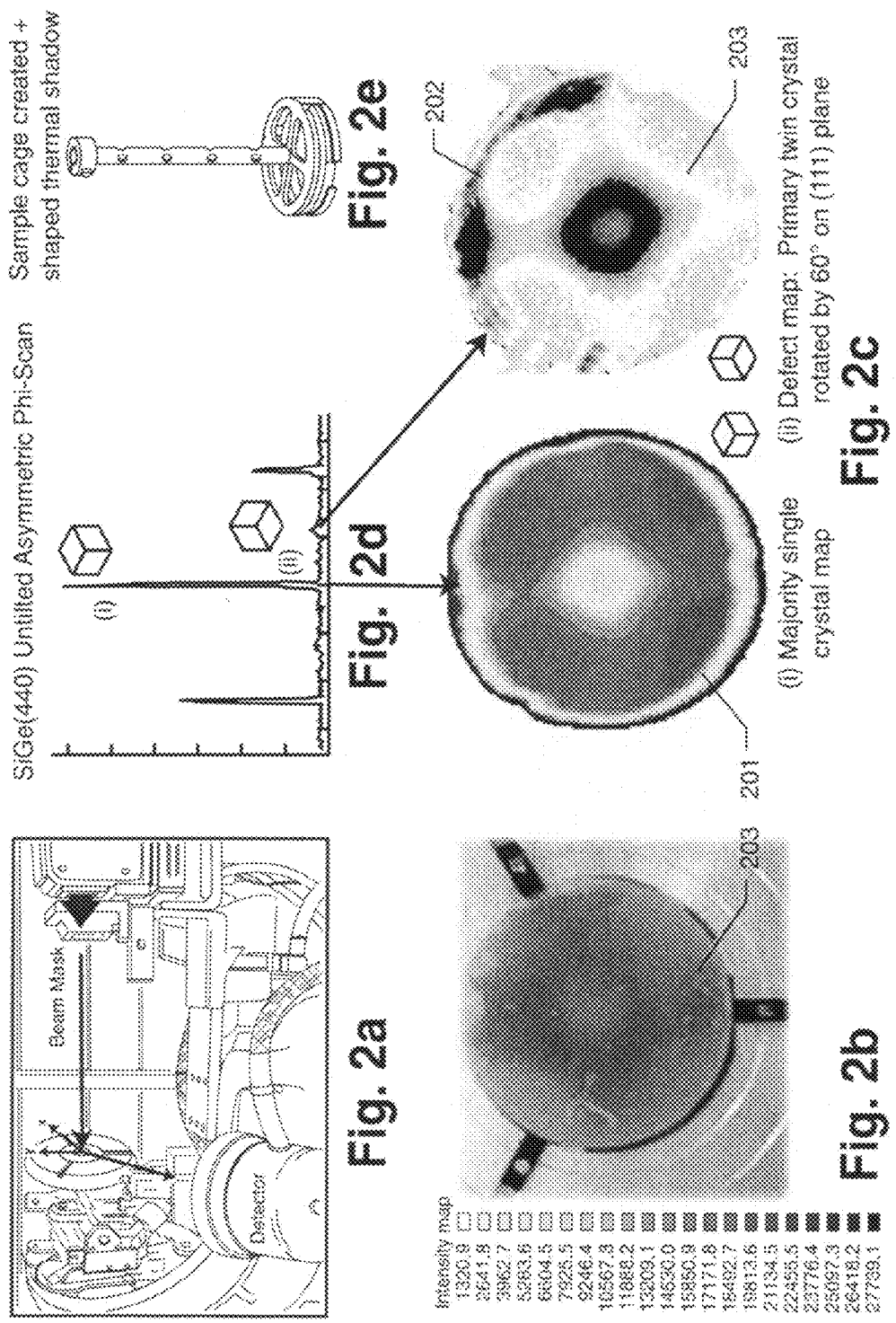
FIG. 2 comprises a set of panels showing (a) an exemplary configuration in accordance with FIG. 1; (b) a photograph of a wafer from a view normal to its face; (c) wafer mapping with a selection of diffraction from un-tilted asymmetric phi-scan of SiGe {440} peaks, for: (i) mapping of majority single crystal region in a wafer, and (ii) mapping of primary twin crystal rotated 60° on the (111) plane region, i.e. the twin defect region in the same wafer; (d) corresponding (440) untilted asymmetric XRD phi scan with point X-ray source, and (e) a perspective view of the sample cage used for these scans. A color version of this figure is included in the reference paper, Y. Park, G. C. King, S. H. Choi, Rhombohedral epitaxy of cubic SiGe on trigonal c-plane sapphire, Journal of Crystal Growth 310 (2008) 2724-2731, which has been incorporated herein by reference in its entirety.

FIG. 2 shows an exemplary wafer mapping result with the described XRD method. FIG. 2(a) shows an exemplary configuration in accordance with FIG. 1. FIG. 2(b) is a photograph of a wafer from a view normal to its face. FIG. 2(c) shows wafer mapping with a selection of diffraction from un-tilted asymmetric phi-scan of SiGe {440} peaks, for: (i) mapping of majority single crystal, and (ii) mapping of primary twin crystal rotated 60° on the (111) plane region, i.e. twin defect region of the same wafer.

Figure 3:
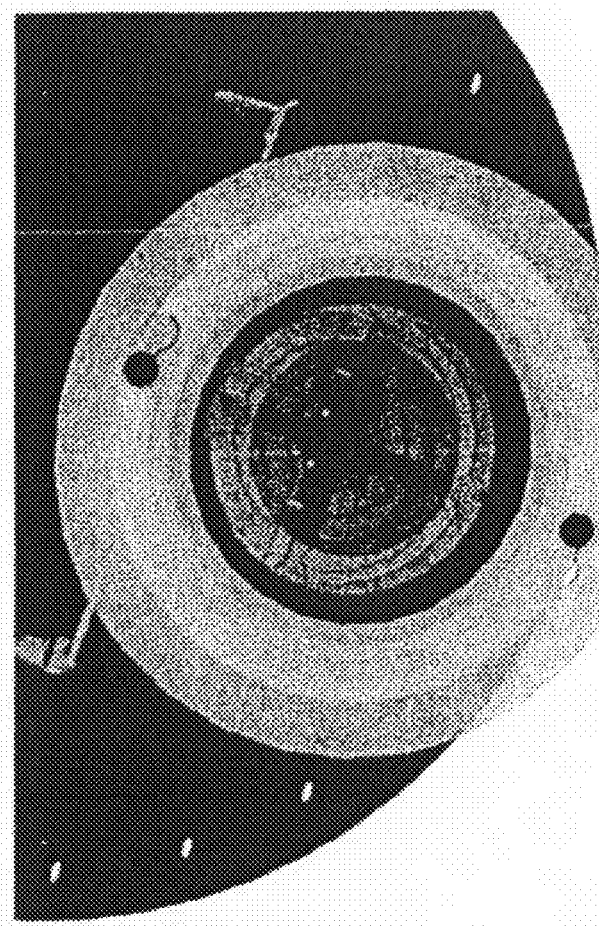
FIG. 3 is a perspective view from the approximate direction of the beam exit, showing the structure of a sample cage in one embodiment.

The un-tilted asymmetric phi-scan 2(d) of SiGe {440} peaks shows three strong single crystalline peaks (i) and weak twin defect peaks (ii). By setting the sample's azimuthal phi(φ) angle to the desired peak (one of the strong single crystal peaks or one of the weak twin defect peaks) and moving the wafer in X and Y direction, we can obtain the XY mapping image of the wafer, as shown as 2(c)(i) majority single crystal map and 2(c)(ii) defect map. While the majority single crystal map 2(c)(i) shows very uniform strong signal all over the wafer 201, the defect map 2(c)(ii) shows a small concentrated region 202 of twin defect at the edge. A weak (+) shaped region of twin defect 203 can be observed in the defect map 2(c)(ii). This distribution of defect was caused by a thermal shadow of our sample cage as shown in FIG. 3. FIG. 2(e) shows a perspective view of the sample cage used for these scans. A color version of this figure is included in the reference paper by the inventors, Journal of Crystal Growth 310 (2008) p. 2724-2731, which has been incorporated by reference herein.

FIG. 4 shows the wafer mapping of another exemplary SiGe layer on c-plane sapphire, and a selection of diffraction from un-tilted asymmetric phi-scan of SiGe {440} peaks. A color version of this figure is included in the reference paper by the inventors, Journal of Crystal Growth 310 (2008) p. 2724-2731. FIG. 4(a) shows XRD normal scan of rhombohedral SiGe oriented in [111] direction on sapphire (0001) plane with a line X-ray source, and FIG. 4(b) shows XRD Phi(φ)-scan of SiGe {440} peaks with a point X-ray source and beam-mask as a pre-measurement for wafer mapping (with 4(b)(1) showing a SiGe (220) tilted Phi-scan, and 4(b)(2) showing a SiGe (440) un-tilted asymmetric Phi-scan). This sample shows single crystalline mirror-like surface FIG. 4(c), and further shows, in FIG. 4(d)(i) and FIG. 4(d)(ii), four quadrant regions 401 and the (+) shaped defect area at the center caused by the sample cage. It is important that the four mirror-like surface regions do not contain twin defects as shown as a low-intensity colored region 402 in the defect map 4(d)(ii). The primary twin defect is concentrated at the low temperature region, (+) shaped thermal shadow region 403 and the edge region 404 in map 4(d)(ii). In accordance with the above, a practical procedure could proceed with the following settings and procedures:

Narrowly defining a point or line X-ray source with a narrow beam mask, slit, or crossed slit. The X-ray spot size on sample is a few nanometers to a few millimeters.

Configuring the XRD apparatus with the following settings:

a. Setting the detector angle (2θ) to approximately the angle of (440) peak. For an example of fully relaxed cubic material, 2θ is given by $$2\theta = 2\cdot\arcsin\left(2\sqrt{2}\cdot\frac{\lambda}{a}\right),$$

where $a$ is the cubic lattice constant, $\lambda$ is the wavelength of X-ray.

If the cubic material is strained, this equation may be modified.

b. Setting sample tilt angle, ψ(or χ) to approximately 0.

c. Calculating the inter-planar angle (τ) between (111) plane and (440) plane (τ=35.264°).

d. Setting the goniometer (sample) angle Ω to approximately θ+τ, where θ is the half of detector angle (2θ). (With above settings, the exit angle of diffracted X-rays becomes θ−τ>0°, which is a measurable validity check.)

Performing a Phi(φ)-scan to find (440) peaks of single crystal and 60° rotated twin defects Setting the Phi(φ) angle to a desired peak (for example, setting Phi(φ) angle to a tiny twin defect peak for defect mapping.)

Moving the sample wafer in the X and Y directions and recording the intensity of diffracted X-ray over this movement to get the wafer mapping.

Displaying the recorded XY mapping and using the data for defect characterization.

Thus, it is apparent that the methods and materials described in the present disclosure satisfy the objects of the invention set forth above. In particular, the above described XRD method provides a useful method for characterizing primary twin defects in rhombohedrally grown cubic semiconductors on the basal plane of trigonal or hexagonal substrate, i.e. rhombohedral super-hetero epitaxy as described in the Rhombohedral Cubic Semiconductor Disclosure. It can be used in the mass production line of a semiconductor wafer process for quality control purposes and sorting out high-quality prime wafers.

The fabrication of a twin-free single-crystalline SiGe layer region with the mirror-like surface shows that the rhombohedral super-hetero epitaxy can make high quality epitaxial layers which are suitable for the delicate device fabrication.

This technique can also be used as an additional characterization tool for materials produced in accordance with the disclosure of our commonly filed patent application entitled "Hybrid Bandgap Engineering for Super-Hetero-Epitaxial Semiconductor Materials, and Products Thereof," Ser. No. 12/254,134, which, as stated above, has been incorporated herein by reference in its entirety. The present disclosure also hereby incorporates by reference the entirety of our recently published article, "Rhombohedral epitaxy of cubic SiGe on trigonal c-plane sapphire", Y. Park et al., Journal of Crystal Growth 310 (2008) 2724-2731.

Although the present invention has been described in detail, it should be understood that various changes, substitutions, and alterations may be readily ascertainable by those skilled in the art and may be made herein without departing from the spirit and scope of the present invention as defined by the following claims.

What is claimed is:

1. A method for X-ray diffraction XY mapping of the distribution crystal forms and defects across a semiconductor wafer comprised of rhombohedrally aligned group IV, group III-V, or group II-VI materials, or alloys thereof, on the (0001) c-plane of trigonal or hexagonal crystal substrate, said method comprising:
  a) providing a point or line X-ray source;
  b) setting the detector angle (2θ) to the angle of a (440) peak of said rhombohedrally aligned material;
  c) setting a sample tilt angle, ψ(or χ) of approximately 0;
  d) calculating the inter-planar angle (τ) between the (111) plane of said rhombohedrally aligned material and said (440) plane;
  e) setting the goniometer angle Ω approximately equal to θ+τ, where θ is the half of detector angle (2θ);
  f) performing a Phi(φ)-scan to find (440) peaks of single crystal and 60° rotated twin defects;
  g) setting the Phi(φ) angle to a desired peak; and
  h) moving the sample wafer in X and Y directions and recording the intensity of diffracted X-rays at the various positions of said movement.

2. The method of claim 1, wherein said X-ray source is directed through an aperture selected from the group consisting essentially of a narrow beam mask, slit or crossed slit.

3. The method of claim 1, wherein said X-ray source is directed through a crossed slit.

4. The method of claim 1, wherein the spot size of said X-ray impinging on said target is in the range of from a few nanometers to a few millimeters.

5. The method of claim 1, wherein said rhombohedrally aligned material is fully relaxed, and said detector angle (2θ) is given by $$2\theta = 2 \cdot \arcsin\left(2\sqrt{2} \cdot \frac{\lambda}{a}\right),$$

where $\alpha$ is the cubic lattice constant, and $\lambda$ is the X-ray wavelength.

6. The method of claim 1, further comprising measuring the exit angle θ–τ of diffracted X-rays and determining whether said angle is greater than 0° as a validity check.

7. The method of claim 1, wherein the Phi(φ) angle is set to a twin defect peak for defect mapping.

8. The method of claim 1, further comprising displaying the recorded XY mapping.

9. The method of claim 1, further comprising using said wafer mapping data for defect characterization.

* * * * *